(12) United States Patent
Andresen et al.

(10) Patent No.: US 6,338,824 B1
(45) Date of Patent: Jan. 15, 2002

(54) METHOD FOR DETECTION OF EXTREMELY LOW CONCENTRATION

(75) Inventors: Brian D. Andresen, Livermore; Fred S. Miller, Bethal Island, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/328,088

(22) Filed: Jun. 8, 1999

Related U.S. Application Data

(62) Division of application No. 08/935,933, filed on Sep. 23, 1997, now Pat. No. 5,980,832.

(51) Int. Cl.$^7$ .......................... G01N 21/00; G01N 21/75
(52) U.S. Cl. ............................. 422/91; 422/83; 422/88; 422/89; 422/78; 422/80; 436/134; 436/104; 436/142; 436/144; 73/23.2; 73/23.22; 73/23.35; 73/23.4
(58) Field of Search ...................... 422/80, 83, 88–89, 422/91, 78; 436/104, 142, 134, 144; 73/23.2, 23.22, 23.35, 23.4

(56) References Cited

U.S. PATENT DOCUMENTS

| 3,420,636 A | * | 1/1969 | Robbins | 23/254 |
| 3,871,827 A | * | 3/1975 | Seiler et al. | 23/254 R |
| 4,309,385 A | * | 1/1982 | Harada et al. | 422/83 |

(List continued on next page.)

FOREIGN PATENT DOCUMENTS

| JP | 06191822 A | * | 7/1994 |
| JP | 08300567 A | * | 11/1996 |

OTHER PUBLICATIONS

Silver, G. M. and Fall, R. "Enzymatic Synthesis of Isoprene from Dimethylallyl Diphosphate in Aspen Leaf Extracts." Plant Physiol. 1588–1591, 1991.*

Prakash, S. S., Brinker, C. J., Hurd, A. J., and Rao, S. M. "Silica Aerogel Films Prepared at Ambient Pressure by Using Surface Derivatization to Induce Reversible Drying Shrinkage." Nature, 439–443 Mar. 1995.*

Cao, X., Hewitt, C. N., Waterhouse, K. S. "Determination of Reactive Hydrocarbons by Capillary Gas Chromatography with the Reduction Gas Detector." J. Chromatog. A., 115–121, Sep. 1994.*

(List continued on next page.)

Primary Examiner—Jill Warden
Assistant Examiner—Kathryn Bex
(74) Attorney, Agent, or Firm—L. E. Carnahan; Alan H. Thompson

(57) ABSTRACT

An ultratrace detector system for hand-held gas chromatography having high sensitivity, for example, to emissions generated during production of weapons, biological compounds, drugs, etc. The detector system is insensitive to water, air, helium, argon, oxygen, and $CO_2$. The detector system is basically composed of a hand-held capillary gas chromatography (GC), an insulated heated redox-chamber, a detection chamber, and a vapor trap. For example, the detector system may use gas phase redox reactions and spectral absorption of mercury vapor. The gas chromatograph initially separates compounds that percolate through a bed of heated mercuric oxide (HgO) in a silica—or other metal—aerogel material which acts as an insulator. Compounds easily oxidized by HgO liberate atomic mercury that subsequently pass through a detection chamber which includes a detector cell, such as quartz, that is illuminated with a 254 nm ultra-violet (UV) mercury discharge lamp which generates the exact mercury absorption bands that are used to detect the liberated mercury atoms. Atomic mercury strongly absorbs 254 nm energy is therefore a specific signal for reducing compounds eluting from the capillary GC, whereafter the atomic mercury is trapped for example, in a silicon-aerogel trap.

12 Claims, 1 Drawing Sheet

U.S. PATENT DOCUMENTS

| | | | | |
|---|---|---|---|---|
| 4,411,867 A | * | 10/1983 | Ostrander | 422/91 |
| 4,889,814 A | * | 12/1989 | Succi | 436/133 |
| 5,209,773 A | * | 5/1993 | Audhe et al. | 75/388 |
| 5,325,016 A | * | 6/1994 | Srivastava | 313/486 |
| 5,382,452 A | * | 1/1995 | Bruno et al. | 427/215 |
| 5,409,683 A | * | 4/1995 | Tillotson et al. | 423/338 |
| 5,525,799 A | * | 6/1996 | Andresen et al. | 250/288 |
| 5,607,496 A | * | 3/1997 | Brooks | 75/670 |
| 5,746,992 A | * | 5/1998 | Yoldas et al. | 423/338 |

OTHER PUBLICATIONS

Klemm, O., Hanh, M., and Giehl, H. "Airborne, Continuous Measurement of Carbon Monoxide in the Lower Troposphere." Environ. Sci. Technol. 115–120, 1996.*

Greenberg, J. P., et al. "Sub–Parts Per Billion Detection of Isoprene Using a Reduction Gas Detector with a Portable Gas Chromatograph." Atmos. Environ. 27A: 2689–2692, Nov. 1993.*

* cited by examiner

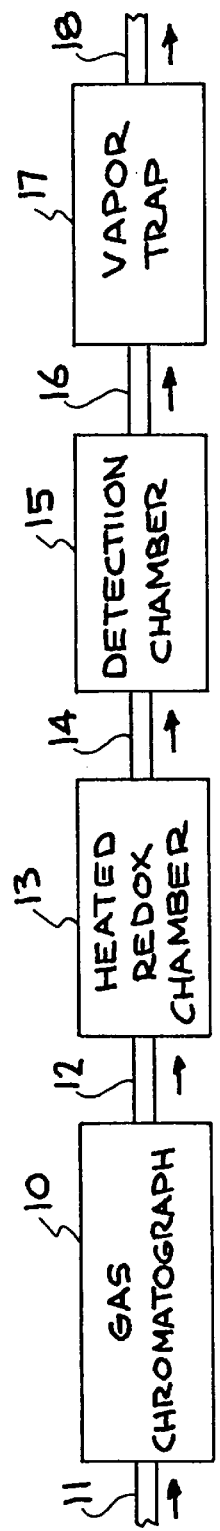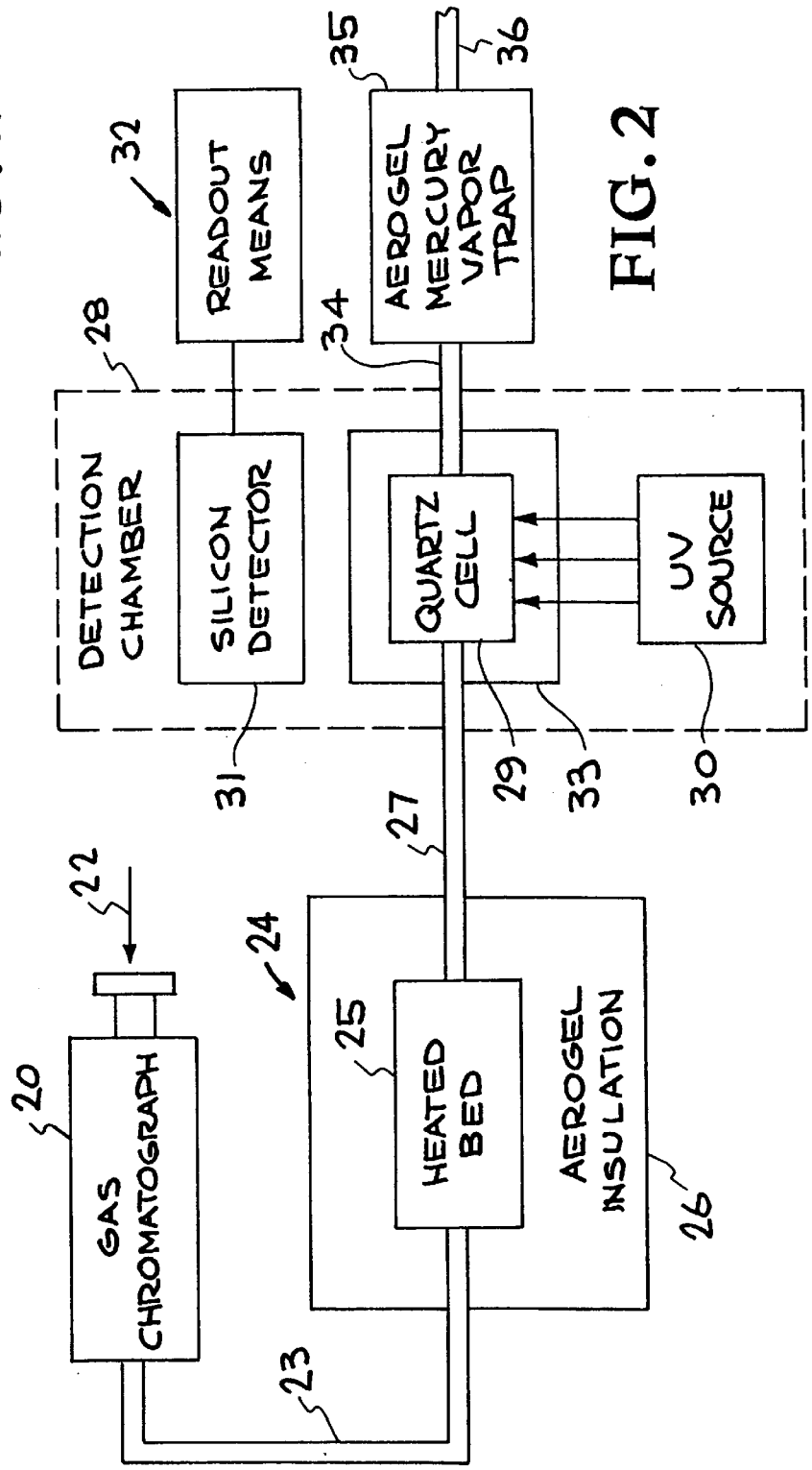

METHOD FOR DETECTION OF EXTREMELY LOW CONCENTRATION

This appln. is a division of Ser. No. 08/935,933 filed Sep. 23, 1997 now U.S. Pat. No. 5,980,832

The United States Government has rights in this invention pursuant to Contract No. W-7405-ENG48 between the United States Department of Energy and the University of California for the operation of Lawrence Livermore National Laboratory.

BACKGROUND OF THE INVENTION

The present invention relates to detector systems, particularly to the detection of extremely low concentrations of emissions or airborne compounds, and more particularly to an ultra sensitive detector for hand-held gas chromatographic analyses of various gases or compounds while being insensitive to other materials.

Emissions generated during manufacturing operations, such as the manufacture of weapons of mass destruction, are generally at extremely low concentrations downwind of any manufacturing facility. In order to support field collections and analysis of such target species in a complex matrix, very sensitive and highly specific analytical tools are required.

Recently, a hand-held (portable) gas chromatographic oven and pancake capillary gas chromatographic column has been developed at the Lawrence Livermore National Laboratory for fast gas chromatographic analysis of industrial gases. However, in order to support field collections and analyses using implace sensors, a new type detector for use in conjunction with gas chromatography, which is both highly specific and extremely sensitive, is needed.

The present invention provides such a ultra-sensitive detector for hand-held gas chromatographic analyses of high explosives (HE), chemical weapons (CW), CW-precursor and CW-hydrolysis compounds, hydrogen (tritium), and other organic compounds, in particular biochemicals biological weapons (BW), signature, for example, while being insensitive to $H_2O$, $N_2$, He, Ar, $O_2$, $CO_2$, and saturated hydrocarbon gases. The key detector of this invention utilizes gas phase redox reactions and spectral absorption of atomic mercury (Hg). Compounds easily oxided by mercuric oxide (HgO) with liberate atomic mercury that subsequently passes through a quartz cell, illuminated with 254 nm ultra-violet (UV) light. Utilizing mercury as the indicator species, this detector is exquisitely sensitive (low femtograms) to target compounds of interest.

SUMMARY OF THE INVENTION

It is an object of the present invention to provide an ultra-sensitive detector for field collection and analysis of manufacture emissions, airborne compounds, etc., collected on a suitable matrix.

A further object of the invention is to provide an ultratrace detector for hand-held gas chromatography of various organo- and organo-metallic compounds, gases, etc.

A further object of the invention is to provide a detector system that is both specific and extremely sensitive.

Another object of the invention is to provide an ultra-sensitive detector arrangement in combination with a hand-held gas chromatograph.

Another object of the invention is to provide a detection and analysis system using a gas chromatograph in combination with a heated redox-chamber, a detection chamber, and a vapor trap.

Another object of the invention is to provide a detector in combination with a capillary gas chromatograph (GC), wherein the GC initially separates compounds that percolate through a bed of heated mercuric oxide in a silica-aerogel material, which liberates atomic mercury that is passed through an ultra-violet detector cell for identification, and thereafter is collected in a vapor trap.

Other objects and advantages of the present invention will become apparent from the following description and accompanying drawings. The invention involves an ultratrace detector for hand-held gas chromatography of target species, such as high explosives, hydrogen gas, biological compounds, drugs, etc. The invention enables detection limits that can approach or exceed femtogram levels for unique compounds in complex mixtures, yet be insensitive to non-reactive compounds such as water, helium, argon, oxygen, carbon dioxide, and saturated hydrocarbon compounds. The invention provides a gas chromatograph/detector system that is small, specific, and extremely sensitive. The detector uses gas phase redox reactions and spectral absorption of liberated mercury vapor. The redox reactions are carried out in a bed of heated mercuric oxide (HgO) in a silica, other mineral bed, or aerogel material which provides insulation for the bed. Compounds oxidized by HgO will liberate atomic mercury that passes through a detector-cell illuminated by a mercury discharge lamp. The liberated mercury atoms are then collected in a small Hg vapor trap. The mercury vapor trap can be used as a detector when properly recharged in a laboratory.

BRIEF DESCRIPTION OF THE DRAWINGS

The accompanying drawings, which are incorporated into and form a part of the disclosure, illustrate an embodiment of the invention and, together with the description, serve to explain the principles of the invention.

FIG. 1 illustrates in block diagram the basic components and operation of the present invention.

FIG. 2 is a schematic illustration of an embodiment of the invention.

DETAILED DESCRIPTION OF THE INVENTION

The invention is directed to a detector for hand-held gas chromatography that is both specific and extremely sensitive to enable field collections and analysis of low concentration levels of target species. The invention is particularly adapted for detection of emissions generated during the manufacture of weapons of mass destruction, such as high explosives (HE), chemical weapons (CW), tritium, and biochemical weapons (BW) signatures, as well as CW-precursors or CW-hydrolysis compounds, and biochemical compounds. In addition the invention is capable of detecting low concentrations (range of $10^{-15}$g to $10^{-18}$g) of biological compounds, drugs, hydrogen, ethylene, hydrogen sulfide, hydrogen cyanide, carbon monoxide, etc. However, the detector is insensitive to non-reactive compounds such as $H_2O$, $N_2$, He, Ar, $O_2$, and $CO_2$, as well as saturated hydrocarbons (gasoline, jet and diesel fuels). Thus, using capillary gas chromatography, the detector can achieve higher detection capabilities than flame photometric (FPD), ion mobility-mass spectrometry, or other prior known detection schemes.

The detector of this invention, used in combination with a gas chromatograph (GC), utilizes redox reactions and the unique spectral absorption bands of mercury vapor. The GC initially separates compounds that percolate through a bed of heated oxidizer material, such as mercuric oxide (HgO) in a silica, other mineral bed, or aerogel material. Compounds easily oxidized by HgO liberate atomic mercury that subsequently pass through a quartz detector cell that is illuminated with a 254 nm ultra-violet (UV) mercury discharge lamp. A mercury lamp generates the exact mercury absorption bands that are used to detect the liberated mercury atoms. Atomic mercury strongly absorbs 254 nm energy and is therefore a specific signal for compounds eluting from the GC, the GC being either a capillary GC column or a hand-held GC silicon waffer instrument, each having been previously developed. Using this approach and instrument design, the detection limits can approach and exceed femtogram levels for unique compounds in complex mixtures, yet be insensitive to certain liquids, gases, and other background compounds. The detector can also be utilized as an implace sensor for specific airborne compounds.

The invention has many uses including: new gas chromatographic detector for industry, drug detection for DEA, very sensitive flammable gas detector, (oil well alarms), chemical and biological weapons monitoring, pollution monitoring, nuclear proliferation signatures, in-line monitoring for gas and oil refineries, solvent monitoring in electronic industries, as well as stack emission control and monitoring.

The detector of this invention preferably uses capillary gas chromatography to achieve higher separations and greater sensitivity. Since the detector is insensitive to water, air, helium, nitrogen, argon, oxygen and carbon dioxide, it can be used as a monitoring device for process control operations where extreme sensitivities are required. Warm up time of the detector is also shorter in that the heated redox-chamber is encapsulated using aerogel materials made of silica, minerals, or other inorganic materials. When the aerogel insulated redox-chamber containing HgO is heated, the target compound to be combined with the mercury oxygen passes through the bed, and the following reaction, for example, will take place: hydrogen is detected as: $H_2 + HgO > H_2O + Hg$ (vapor). Since a portable unit must be energy efficient, the heated reaction or redox-chamber utilizes the highly efficient insulation properties of the aerogel material to maintain a constant temperature and prevent heat loss. This will ensure longer power supply (battery) life for a hand-held (portable) detector system. Silica, other mineral, or aerogel material, aside from its insulation characteristics for the reaction chamber, is also used for post detection collection to chemically react with and absorb the liberated Hg vapor generated from the gas phase redox reaction. The aerogel material thus functions as a vapor trap following detection of the species in the quartz detection chamber.

The aerogel materials may be composed of mercury-based (Hg) aerogels which have been prepared and tested for the redox-chamber and post reaction collection (vapor trap). A variety of silica-mercury and metal-based aerogel materials are being considered for use in the detector system of this invention. These include metal-salt aerogels for sensors and molecular—engineered fiber—impregnated aerogels for sample collectors and effluent filtration devices. The present invention combines previous expertise with aerogels, and the thermally robust nature and special characteristics of metal and salt-impregnated (and coated) aerogels to allow for an extremely sensitive detector for unique target compounds in complex mixtures. Thus, femtogram (and lower) sensitivities of trace airborne compounds can be detected that will aid nonproliferation activities and preserve national security, as well as industrial pollution monitoring.

Referring now to the drawings, FIG. 1 shows in block diagram the basic compounds and operation of a detector system made in accordance with the present invention.

The detector system, as illustrated in FIG. 1, basically comprises a gas chromatograph 10 having a sample inlet 11 and a reaction outlet 12 directed into a heated redox-chamber 13, the output of chamber 13 indicated at 14 being directed to a detection chamber 15, with the output of detection chamber 15 indicated at 16 being directed into a vapor trap 17 with exhaust therefrom indicated at 18.

FIG. 2 illustrates an embodiment of a detector system utilizing heated mercuric oxide in the redox-chamber (13) and a quartz detector cell illuminated with a small mercury discharge lamp in the detection chamber (15), and which utilizes an inorganic aerogel (silica or other metal) in the redox-chamber (13) and in the vapor trap (17). The gas chromatography (GC) (10) may, for example, be a portable (hand-held) gas chromatographic oven and pancake capillary chromatographic column, developed at the Lawrence Livermore National Laboratory, and described in U.S. Pat. No. 5,525,799. This GC could be used in the detection of various compounds indicative of biologic organisms of interest, high explosives (HE), chemical weapons (CW) agents, aroma signatures of biological weapons (BW), biological compounds, drugs, and carbon monoxide. Utilizing mercury as the indicator species in the redox-chamber and detection chamber, this detector is exquisitely sensitive (low femtograms) particularly to hydrogen, ethylene, hydrogen sulfide, hydrogen cyanide, etc., while being insensitive to compounds such as $H_2O$, $N_2$, He, Ar, $O_2$, $CO_2$, and saturated hydrocarbon gases (gasoline, jet and diesel fuels).

As shown in FIG. 2, a capillary GC 20 having an inlet 21 into which samples are injected as indicated at 22, and the GC peaks are directed by line or outlet 23 into a heated redox-chamber 24 and allowed to percolate through a heated bed 25 of mercuric oxide (HgO) surrounded by aerogel insulation 26 forming in redox-chamber 24. Compounds easily oxidized by HgO liberate, atomic mercury that subsequently passes via line 27 to detection chamber 28, wherein it passes through a photodetector, such as quartz cell 29 illuminated with 254 nm ultra-violet light from a source 30, such as a mercury vapor lamp. Atomic mercury strongly absorbs 254 nm light and thus produces a specific signal which is detected by a silicon detector 31, for example, which produces an output signal for a readout means, generally indicated at 32. The quartz cell 29 is insulated as indicated at 33 with silica aerogel, for example, to prevent heat loss, save energy, and allow the mercury vapor to pass completely through the detection chamber 28. After passing through the detection chamber 28, the liberated mercury passes through line 34, is subsequently trapped in a vapor trap 35 constructed of a bed of aerogel material chemically designed to capture and hold any mercury compounds, with non-mercury materials passing through exhaust line 36.

In order to optimize the HgO bed, reduce the size of the detector mercury-based aerogel materials have been utilized in the HgO bed of redox-chamber 24. Aerogels, (silica—or other metals) are now well known in the art, and constitute a class of low density solid foams that are characterized by open cell structures composed of silicon and metal salt particles with pore sizes in the range of 4–500 nm in diameter. These inorganic aerogels can be transformed into different chemical compositions by altering the sol-gel chemistry during fabrication. A variety of silica-aerogels and mercury-salt matrices that optimize the detection of target compounds may be used. For example, metal salt impregnated and fiber-based aerogels are being developed for sample collection and effluent filtration. The application disclosed herein takes advantage of the thermally robust aerogel material in a heated detector as well as the ability to have the chemistry of the aerogel be modified for detection of specific target species.

The detector of this invention is small, highly sensitive, and has few external components. Gas chromatographic separation of the reducing compounds may be accomplished using a gas chromatographic oven (7"×6"×1.5") containing a coiled 15 meter capillary column on a pancake heater. Separated compounds are carried into a small bed (100 mg) of heated mercuric oxide-aerogel. The chemical compound is immediately oxidized, releasing mercury vapor that is detected with a miniature mercury vapor lamp and UV sensitive photodiode. The liberated mercury is subsequently trapped in a bed of aerogel chemically designed to capture and hold any mercury compounds.

Since a variety of other metal species can be placed in the thermally stable aerogel matrix, other possible designs for specific target compounds are being investigated. For example, mixed redox reaction can be optimized to detect tributylphosphate (TBP), drugs, or other proliferent signatures. The detector of this invention can also be designed as a stand alone monitor for reducing compounds. Thus, it has been shown that the detector of this invention is highly specific, extremely sensitive to compounds of interest in complex matrices, and can be utilized in field operations for the detection of extremely low concentrations of fugitive emissions, such as those generated in the manufacture of weapons of mass destruction, as well as use as an implace sensor for specific airborne compounds.

While a particular embodiment, materials, parameters, etc., have been illustrated and/or described to exemplify and teach the principles of the invention, such are not intended to be limiting. Modifications and changes may become apparent to those skilled in the art, and it is intended that the invention be limited only by the scope of the appended claims.

What is claimed is:

1. A method for detecting concentrations in the range of $10^{-15}$ g/unit time to $10^{-18}$ g/unit time of a target species in a sample gas, comprising:

providing a gas chromatograph, directing the sample gas through said gas chromatograph to separate the target species, providing a heated redox-chamber including an aerogel material and containing a bed of mercuric oxide, connecting the heated redox-chamber to the gas chromatograph to allow the sample gas containing the separated target species to percolate through the bed of mercuric oxide causing oxidizing of the target species and liberation of mercury atoms from the bed, providing an ultra-violet light detection chamber having an ultra-violet sensitive detector and a source of ultra-violet light, directing the liberated mercury atoms through the detection chamber for detection thereof by the detector, correlating the detected mercury atoms to the concentration of the target species providing a vapor trap having an aerogel material, and directing the liberated mercury atoms into the vapor trap to trap the mercury atoms therein.

2. The method of claim 1, additionally including providing the bed of the redox-chamber with an aerogel material.

3. The method of claim 1, additionally including providing the heated redox-chamber with insulation.

4. The method of claim 1, wherein providing the ultraviolet light detection chamber additionally includes providing a quartz cell, and surrounding the quartz cell with an aerogel.

5. A method for detection of femtogram and lower concentration of emissions and airborne compounds in a sample gas, comprising:

providing a gas chromtograph, directing the sample gas through said gas chromatograph to separate said compounds, providing a heated redox-chamber containing an aerogel material and a bed of mercuric oxide, connecting the heated redox-chamber to the gas chromatograph causing oxidizing of said compounds from the gas chromatograph and liberation of mercury atoms from the bed, providing an ultra-violet detection chamber, connecting the detection chamber to the heated redox-chamber, directing the liberated mercury atoms through the detection chamber for detection thereof, correlating the detected mercury atoms to the concentration of said compounds, providing a vapor trap containing an aerogel material, and directing the liberated mercury atoms into the vapor trap to trap the mercury atoms therein.

6. The method of claim 5, wherein providing a gas chromatograph is carried out by providing a portable gas chromatographic oven and a pancake capillary gas chromatographic column.

7. The method of claim 5, wherein providing the detection chamber is carried out by providing a quartz cell, a source of ultra-violet light, a silicon detector, and a signal output readout means, whereby the ultra-violet light is directed through the quartz cell.

8. The method of claim 5, additionally including surrounding the bed of mercuric oxide with an insulator.

9. The method of claim 8, additionally including forming the insulator from aerogel material.

10. The method of claim 5, additionally including depositing the mercuric oxide in cells of the aerogel material contained in the heated redox-chamber.

11. The method of claim 5, wherein providing an ultra-violet light is carried out using a 254 nm ultra-violet light.

12. The method of claim 11, wherein the 254 nm ultra-violet light is produced by a mercury vapor lamp.

* * * * *